United States Patent [19]
Marcove et al.

[11] Patent Number: 5,976,105
[45] Date of Patent: Nov. 2, 1999

[54] INTRA ANNULAR ULTRASOUND DISC APPARATUS AND METHOD

[76] Inventors: Ralph C. Marcove, 200 Old Palisade Rd. Apt. 15G, Fort Lee, N.J. 07024; Philip R. Casson, 18 Shore Dr., Portchester, N.Y. 10573; Charles D. Kelman, 721 Fifth Ave., New York, N.Y. 10022

[21] Appl. No.: 08/811,196

[22] Filed: Mar. 5, 1997

[51] Int. Cl.$^6$ ................................................. A61M 31/00
[52] U.S. Cl. .............................................................. 604/49
[58] Field of Search ................................. 604/22, 49, 164, 604/264, 280, 53; 606/53, 60, 61, 79, 80–86, 105, 167

[56] References Cited

U.S. PATENT DOCUMENTS 5,772,627  6/1998  Acosta et al. .

Primary Examiner—John D. Yasko
Assistant Examiner—Manuel Mendez
Attorney, Agent, or Firm—Darby & Darby

[57] ABSTRACT

An improved method and apparatus for treating herniated discs involving the preliminary intra annular ultrasonic softening of the herniated disc portions to be removed with a discectomy instrument that suctions and cuts the softened portions of the herniated disc. An ultrasonic probe is inserted into the central region of the disc to soften the desired region. A discectomy instrument is subsequently inserted into the softened portion of the disc and tissue is removed by suctioning the softened tissue portion into the tip of the instrument needle and severing the suctioned portion of the disc within the tip of the needle. The cut material is then aspirated.

10 Claims, 3 Drawing Sheets

INTRA ANNULAR ULTRASOUND DISC APPARATUS AND METHOD

BACKGROUND OF THE INVENTION

The present invention relates, generally, to an apparatus and method for treating herniated discs. More particularly, the present invention relates to an ultrasound method and apparatus for first softening a damaged disc region before removing the portion of the disc causing pain. The removal of the softened herniated disc material is preferably done with a Nucleotome® system as described herein.

A herniated disc causes the patient pain by applying pressure against spinal nerves. For over thirty years, the surgical approach has involved open surgical procedures. However, such procedures may be accompanied by complications, such as damage to ligaments, lamina, and the vertebral joints, irritation of the dural sac or nerve roots, as well as occasional post-operative hematoma even infection and formation of the scar tissue. Microsurgical techniques have been used since around 1975. Although microsurgical techniques reduce the overall surgical trauma suffered by the patient, highly specialized instruments must be used In combination with a microscope. Thus, microsurgical techniques are much more intricate, time-consuming, and stressful than open surgical procedures.

One open nonsurgical method of treating herniated discs is shown in U.S. Pat. No. 5,458,596 to Lax et al. This method uses radio frequency or other forms of energy to shrink collagen connective tissue. However, such methods have not proven to be very effective. Moreover, this method treats the disc at the dorsal exterior of the disc outside the annulus and, therefore, increases the risk of damaging the adjacent spinal cord or spinal nerves. It is not used or reported in any substantial series of cases.

Another nonsurgical method of treating herniated discs is the use of chymopapain and chemonucleolysis. However, injection of chymopapain into the lumbar nucleus pulposus may be accompanied by such complications as hypersensitivity to the drug (i.e., allergic reactions, which may result in anaphylaxis), transverse myelitis, subsequent paraplegia, and even death. A popular current method of treating lumbar disc herniation involves the use of a discectomy system manufactured by Surgical Dynamics and sold under the trademark Nucleotome® System. This system involves insertion of a guide pin trocar into the area to be treated, and subsequent insertion of a cannula with a tapered dilator over the guide pin. A trephine is placed over the guide pin and through the cannula and rotated to create an incision through the annulus into the disc. The trephine and guide pin are then removed, leaving the cannula in place. Next, a Nucleotome® probe is inserted into the cannula. The probe suctions a portion of the disc into the probe's hollow interior, where the disc is cut and suctioned away. Complications such as clogging of the probe and removal of an inadequate amount of disc material may occur.

While the use of ultrasonically vibrated tools for aspirating various tissues is known in the art, they have not been applied to the removal of herniated disc material within the annulus fibrosis. Current discectomy methods either disintegrate portions of the disc, or suction portions of the disc, which is often difficult because of the consistency of the disc material. With currently known procedures, a Dong tube (the Nucleotome®) is inserted within the annulus into a damaged disc region and small pieces of disc material are drawn out through the tube by a stream of fluid aspirated into the region and a vacuum applied to suction material out of the region. The vacuum sucks a small amount of disc material into the tube, where it is sliced off by a cutting blade with a guillotine-like action. Water running through the tube flushes the material out. The cycle is repeated until an adequate amount of disc is removed which reduces the pressure on the spinal nerve(s) or spinal cord, or both, depending on the area being treated.

U.S. Pat. No. 3,589,363 to Banko et al. shows the use of an ultrasonically vibrated instrument for disintegrating unwanted tissue, such as a cataracted lens, in an eye. A first passage in the instrument is provided for carrying treatment fluid to the region to be treated, and a second passage is provided for carrying a suspension of unwanted material in the treatment fluid away from the treated area. Additionally, U.S. Pat. Nos. 4,016,882 and 4,136,700 to Broadwin et al. also show the use of an ultrasonically vibrated tool for disintegrating or comminuting soft tissue which is then aspirated through the hollow tip of the device. The tube is vibrated transversely with respect to the longitudinal axis of the tip and to the direction of contact. Ultrasonic vibration is accompanied by simultaneous aspiration. The disclosed device may allegedly be used to excise spinal column tumors.

Another use of an ultrasonically vibrated instrument is shown in U.S. Pat. No. 5,167,619 to Wuchinich. The Wuchinich instrument is allegedly usable to melt cement in a bone without affecting the integrity of the bone. The melted cement material is said to be drawn into the tip by applied suction. The tip may also be rotated so that the cement is exposed to shearing as well as axial vibration.

SUMMARY OF THE INVENTION

It is a principal object of the present invention to provide an improved method and apparatus for treating a herniated disc.

A related object of the invention is to provide an apparatus and method for making removal of herniated disc material simpler and easier.

Another related object of the present invention is to provide a new use for ultrasonically vibrated instruments, wherein the instrument is used to soften a herniated disc within the annulus fibrosis to thereby facilitate removal of portions of the disc to alleviate pressure and pain.

In accordance with the principles of the present invention, an ultrasonically vibrated instrument is used to soften the tissue of a herniated disc to facilitate subsequent removal of the softened portion of the disc to alleviate pressure caused by the expanded disc on the patient's spine. Once the disc material is softened, a discectomy needle (Nucleotome®) may be applied to the affected area to cut and remove the desired portion of the herniated disc. Ultrasonic softening makes suction of the disc material for removal easier.

These and other features and advantages of the present invention will be readily apparent from the following detailed description of the invention taken in conjunction with the accompanying drawings, wherein like reference characters represent like elements.

BRIEF DESCRIPTION OF THE DRAWINGS

FIG. 3 shows the ultrasonic instrument inserted to soften the disc material;

DETAILED DESCRIPTION OF THE INVENTION

Figure 1:
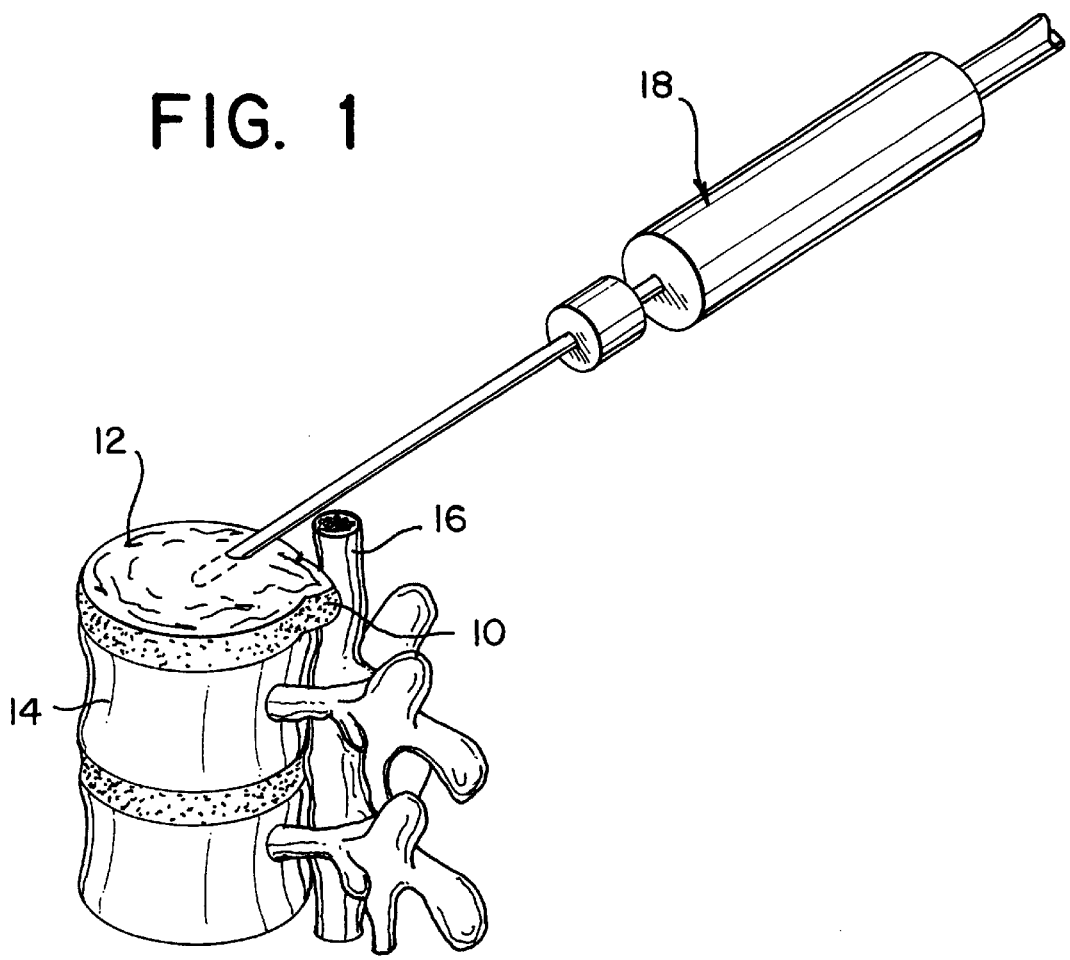
FIG. 1 is an isometric view of an ultrasonic probe according to the present invention, being inserted into a herniated disc to alleviate pressure on the spinal nerves caused by the herniated region of the disc.

The present invention provides a relatively non-invasive surgical approach for treating herniated discs, particularly one that does not unduly traumatize the portion of the disc that is to be left intact. In accordance with the principles of the present invention, the central region of a herniated disc is first softened by an appropriate ultrasound instrument, and then a portion of the softened material is removed to relieve pressure caused by the herniated portion of the disc against the spinal nerves, or spinal cord, or both, depending on the area being treated. As may be seen in FIG. 1, the herniated portion 10 of disc 12 extends beyond the normal circumference wall of the body of the vertebra 14 (in this situation, the herniated disc is in the lumbar region of the vertebral column) and presses against spinal nerves 16, causing discomfort to the patient. Because the ultrasonic treatment tip of instrument 18 is placed substantially at the center of disc 12, there is no risk of injury to the spinal nerves 16 during treatment (as may occur with prior art methods which treat the disc externally), and thus adjacent spinal cord injury 16 is minimized.

Figure 2:
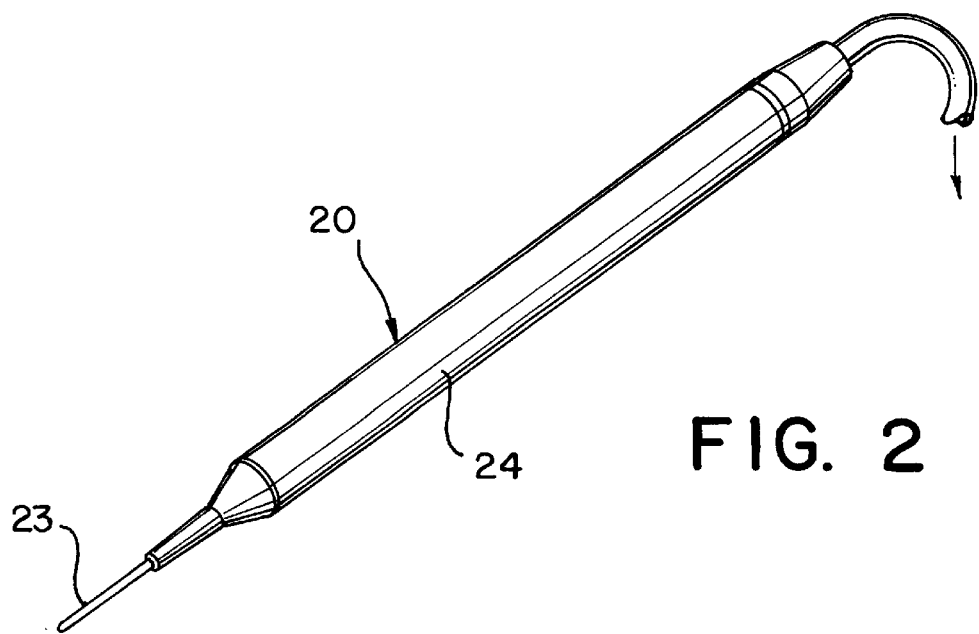
FIG. 2 is an elevational view of an ultrasonic surgical instrument according to the present invention.

In accordance with the principles of the present invention, an ultrasound surgical instrument or probe 20, such as shown in FIG. 2, and having vibration generating apparatus similar to that described in previously-mentioned U.S. Pat. No. 3,589,363 to Banko et al., which patent is hereby incorporated herein by reference in its entirety, is used to soften disc material. Ultrasonic probe 20 typically is approximately 10 inches (25.4 cm) long and approximately 27 mm wide. Ultrasonic probe 20 is inserted into a central region of the herniated disc (as is instrument 18 in FIG. 1) to soften the disc material and thereby facilitate removal of some of the disc tissue to thereby reduce disc pressure on the patient's spinal nerves. Because the ultrasonic probe 20 is adapted for use in a spinal disc, the tip 22 of probe 20, according to the present invention, is substantially longer in length than that of the eye surgery Banko device. Thus, tip 22 is preferably approximately 2 centimeters in length so as to be capable of extending from just outside the patient's annulus into the center of the disc 12 being treated. The tip 22 has a diameter of preferably approximately 1–2 mm, and most preferably approximately 1.2 mm. Tip 22 may be sharp, flat (spatula type), rounded, or any other desired shape that accomplishes the purposes of the present invention. Ultrasonic energy is applied to the tip 22 of the probe 20 by a transducer in the handpiece 24 for vibrating tip 22 longitudinally to soften the disc material, in particular the mucopolysaccharide and collagen of the disc. Tip 22 should be vibrated at a frequency and amplitude necessary to soften body fibrous tissue, such as within disc material, without liquefying the material, as may be determined by one of ordinary skill in the art. A typical range of frequencies is from 25 Khz–60 Khz. The typical amplitude (i.e., distance of travel of the tip from peak to peak of each longitudinal vibration) is 3 mils. Because the ultrasonic energy creates heat, preferably irrigation is provided, as shown in the above-mentioned Banko patent. Because the disc material is softened, subsequent removal by a second treatment instrument such as a Nucleotome® needle is facilitated.

Figure 3A:
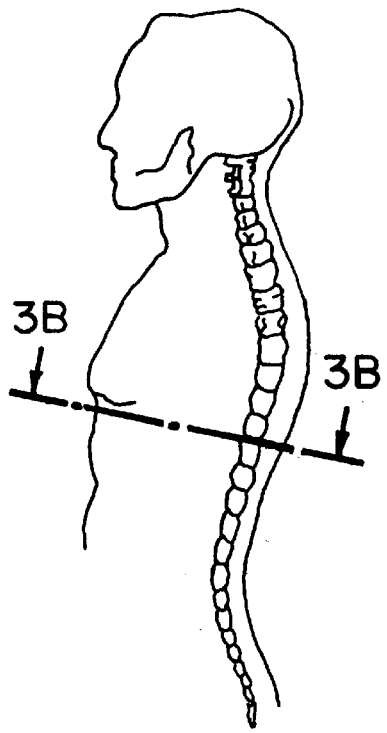
FIG. 3 is a cross-sectional view of a patient having a herniated disc being treated with the method according to the present invention, specifically.
Figure 3B:
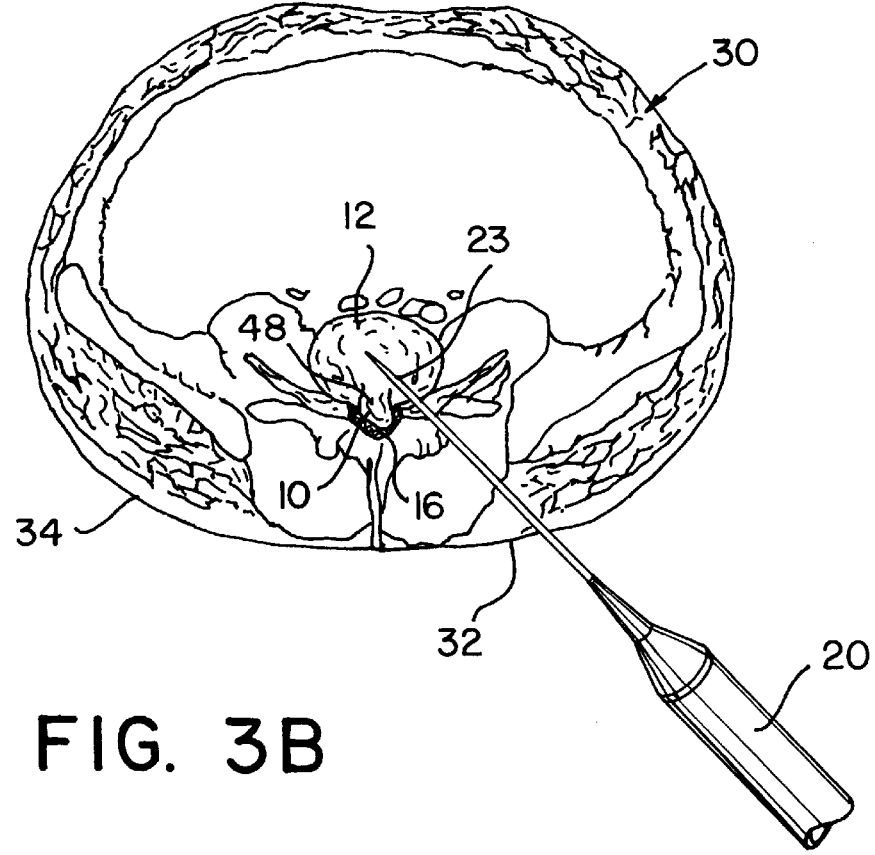

The method of insertion of the ultrasonic surgical instrument 20 of the present invention into the patient will now be described. A cross-section view of a patient 30 is shown in FIG. 3. It will be understood that the second instrument to be inserted is a cutting and suctioning instrument 40 (FIG. 4) (such as a Nucleotome® needle). That instrument is inserted in a similar manner as ultrasound instrument 20 and FIG. 3 could just as easily represent the method of insertion of instrument 40. The entry point of ultrasonic probe 20 through skin 32 of the patient's back 34 is determined radiologically, and preferably is approximately 10 centimeters from the midline of the spine.

The steps taken in preparation for inserting the tissue softening and removal instruments may be performed in any desired manner. As will be understood, the area to be treated must first be prepared by sterilizing the area and then creating an appropriate small stab wound incision approximately 3.5 mm wide in the patient's skin 32 adjacent the herniated disc to be treated and through which the treatment apparati are to be inserted (FIG. 3). The incision may be formed according to any desired surgical procedure. For instance, a guide wire, a tissue dilator, and a rasp (trephine) may be used in the known manner to expand and cut annular tissue from the treatment area.

Once the incision is formed, the tip 22 of the ultrasonic probe 20 is inserted into the patient. Since it is preferable to remove disc material from near the center of the disc, the tip 22 of the ultrasonic probe 20 preferably is inserted into the center of the disc 12 being treated to soften the central region of the disc. Thus, the portion of the disc closest to the spinal nerve 16 is not directly contacted by either the ultrasonic probe or the discectomy needle described below.

Figure 4:
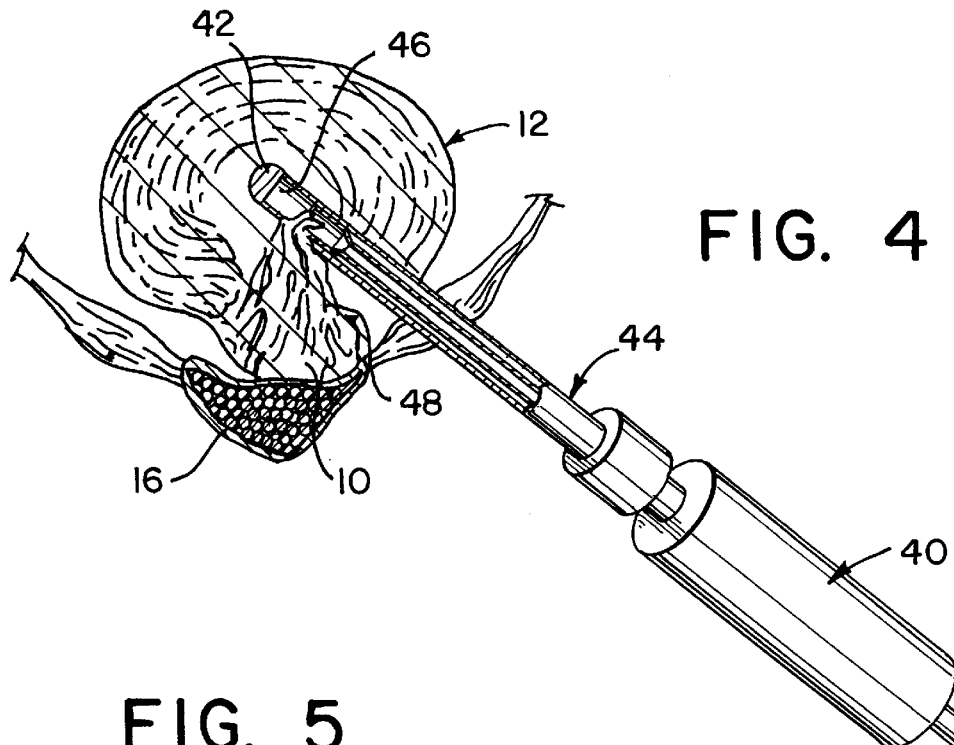
FIG. 4 is an enlarged detail of the disc shown in FIG. 3, but showing removal of softened herniated disc material with a discectomy instrument.
Figure 5:
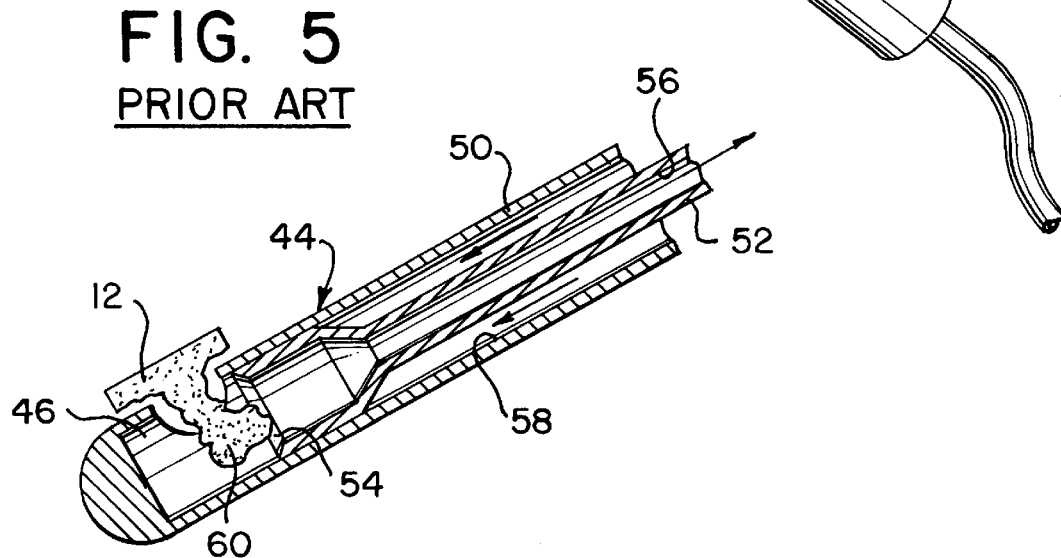
FIG. 5 is a simplified cross-sectional partial view of a prior art discectomy instrument being used to cut and suction a herniated disc.
Figure 6:
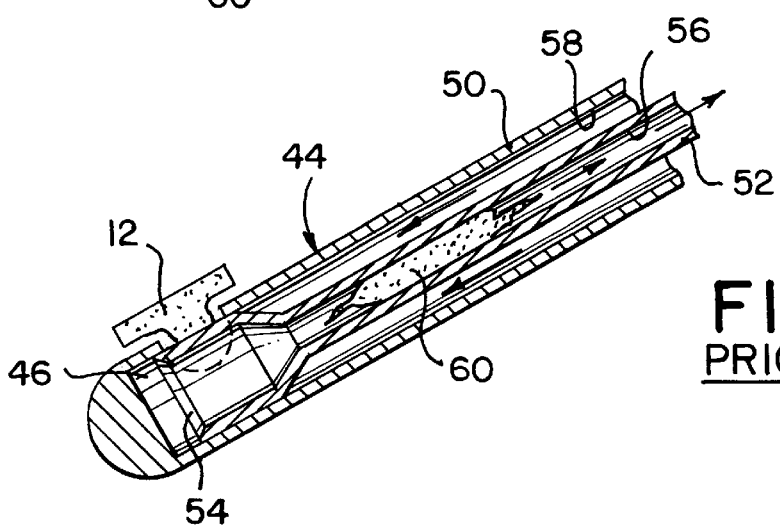
FIG. 6 is a view similar to that of FIG. 5, but at a more advanced stage of treatment.

Once the desired portion of the disc 12 to be treated has been softened by the ultrasonic probe 20, the tip 22 of the ultrasonic probe 20 is removed and a discectomy instrument 40 inserted inside the interior of the annular ligament. Discectomy instrument 40 preferably is a Nucleotome® probe manufactured by Surgical Dynamics. As seen in FIG. 4, instrument 40 is inserted into disc 12 such that distal tip 42 of discectomy instrument 40 is substantially in the center of disc 12 so that, as described above, disc removal is not performed immediately adjacent the spinal nerves. That area can shrink as central disc tissue is removed. Discectomy instrument 40 preferably has a hollow needle 44 with hollow distal tip 46 (preferably approximately 3.2 mm wide, although tips having a diameter of 2, 2.5, 3.5 or 4.7 mm may alternatively be used) positioned adjacent the softened portion 48 of herniated portion 10 of disc 12. As may more clearly be seen in FIGS. 5 and 6, needle 44 preferably has an outer tubular member 50, and an inner tubular member 52 ending in a guillotine-like cutting blade 54. A vacuum is applied within lumen 56 of inner tubular member 52 to provide suction at the distal end. Additionally, a stream of water, or other treatment fluid, is passed through an annular passage lumen 58 between outer tubular member 50 and inner tubular member 52 of discectomy instrument 40 in the direction of the arrows shown in FIG. 5. The water or treatment fluid flushes the treatment site and also causes the tissue that has been softened by the ultrasound instrument to be directed into hollow distal end region 46 of discectomy instrument 40 and suctioned by the vacuum within lumen 56, as shown in FIG. 5. Inner tubular member 52 is longitudinally, i.e., axially, movable with respect to outer tubular member 50, and either may be intermittently regularly moved back and forth, or may be moved at predetermined intervals controlled by the surgeon. When inner tubular member 52 moves towards the distal tip 42 of instrument 40, blade 54 cuts from the remaining portion of disc 12, the portion 60 of disc 12 that has been suctioned into hollow distal end region 46. Thus, tissue 60 is cut, with a guillotine-like action, from the remaining portion of disc 12. The cut portion 60 of disc 12 is suctioned, by the vacuum applied within lumen 56, along with the water or treatment fluid, to a collection vessel.

The above steps of suctioning, severing and removing softened disc material are repeated until sufficient disc material is removed to relieve the pressure on the patient's spinal nerves.

Accordingly, the present invention permits effective and quick treatment of one of the most common debilitating injuries, so that the patient can often go back to work on the same day. The softening of the disc material to be removed, facilitates suctioning and directing of the material into the probe member that cuts and removes the disc tissue from the herniated region. Thus, the softening of the tissue permits the previously used procedures to be accomplished in a substantially shorter amount of operative time, with more efficient and successful removal of the remaining portion of the disc.

While the foregoing description and drawings represent the preferred embodiments of the present invention, it will be understood that various additions, modifications and substitutions may be made without departing from the spirit and scope of the present invention as defined in the accompanying claims. In particular, it will be clear that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. A method of treating a herniated disc comprising the steps of:
    inserting the tip of a first instrument into the central region of a herniated disc to be treated;
    ultrasonically vibrating said tip of said first instrument to soften the central region of the disc;
    removing said tip of said first instrument from the central region;
    inserting the tip of a second instrument into the softened portion of the central region of the herniated disc, said tip of said second instrument having an interior lumen;
    suctioning a portion of the previously softened disc portion into said interior lumen of said second instrument;
    severing the suctioned portion in the interior lumen from the remaining portion of the disc;
    removing the severed portion through said interior lumen of said second instrument; and
    removing said tip of said second instrument from the softened central region of the disc.

2. A method as in claim 1, wherein said tip of said first instrument is elongated and said vibrating step comprises vibrating said tip of said first instrument longitudinally.

3. A method as in claim 1, wherein said tip of said first instrument is at the end of an elongated needle of a length sufficient to permit said tip of said first instrument to reach the central region of the disc.

4. A method as in claim 1, wherein said step of removing the severed portion comprises applying suction to said interior lumen.

5. A method as in claim 4, wherein said step of severing comprises cutting with a movable blade in said second instrument the portion of the disc softened by said first instrument.

6. A method as in claim 5, wherein said second instrument is formed from first and second tubular members concentrically positioned within each other, said inner tubular member including said moveable cutting blade.

7. A method as in claim 1, further comprising the step of applying a stream of fluid through said tip of said second instrument to the softened disc to move a portion of the disc into said lumen.

8. A method as in claim 1, wherein said steps of suctioning, severing, and removing are sequentially repeated until sufficient disc material has been removed to relieve the pressure on the spinal cord.

9. A method as in claim 1, wherein said tip of said first instrument is hollow.

10. A method as in claim 1, further comprising the step of inserting a guide pin into the region to be treated and inserting said first instrument over said guide pin.

* * * * *